United States Patent [19]

Tuckman et al.

[11] Patent Number: 5,338,664
[45] Date of Patent: Aug. 16, 1994

[54] ASSAY FOR DETECTION OF BACTERIAL IRON TRANSPORT INHIBITORS

[75] Inventors: Margareta K. Tuckman, Tenafly, N.J.; Marcia S. Osburne, Lexington, Mass.

[73] Assignee: American Cyanamid Company, Wayne, N.J.

[21] Appl. No.: 985,972

[22] Filed: Dec. 4, 1992

[51] Int. Cl.$^5$ .......................... C12Q 1/10; C12N 1/00
[52] U.S. Cl. .......................................... 435/4; 435/5; 435/32; 435/38; 435/252.33; 435/848; 435/849; 530/330; 514/17
[58] Field of Search .............. 435/4, 5, 32, 38, 252.33, 435/848, 849; 530/330; 514/17

[56] References Cited

PUBLICATIONS

Tuckman et al, *Chemical Abstracts*, vol. 116, p. 403, Ref. #102590y, 1992 (J. Bacteriol. 1992, 174(1), 320–323).
Sauer et al, *J. Bacteriol*, vol. 169, No. 5, pp. 2044–2049, May 1987.
Benedetti et al, *The EMBO Journal*, vol. 10, No. 8, pp. 1989–1995, 1991.
Mann et al, *FEMS Microbiology Letters*, vol. 33, pp. 255–260, 1986.
Schramm et al, *J. Bacteriol*, vol. 169, No. 7, pp. 3350–3357, Jul. 1987.
Fekete et al, *Appl. Env. Microbiol*, vol. 55, No. 10, pp. 2720–2722, Oct. 1989.

*Primary Examiner*—Michael G. Wityshyn
*Assistant Examiner*—Abdel A. Mohamed
*Attorney, Agent, or Firm*—Estelle J. Tsevdos

[57] ABSTRACT

The present invention relates to a method for identifying a TonB inhibitor in a test sample comprising:
(a) growing a TonB$^+$ microorganism in the presence of the test sample and a lethal agent, the activity of which is mediated by TonB;
(b) identifying as positive a test sample with which the lethal activity of the agent is not observed;
(c) growing on a low-iron medium a TonB$^+$ microorganism in the presence of the test sample identified as positive in (b);
(d) confirming as positive a test sample with which growth inhibition of the microorganism is observed on a low-iron medium.

9 Claims, No Drawings

ASSAY FOR DETECTION OF BACTERIAL IRON TRANSPORT INHIBITORS

Although iron is an abundant element, iron-deficiency in organisms is a common problem due to the fact that iron is poorly soluble at physiological pH and is therefore relatively unavailable. The majority of iron in mammalian systems is found as heme. Two other proteins, ferritin, found in the liver, and hemosiderin, are the major intracellular storage forms of iron. Extracellular iron is bound to the two high-affinity iron-binding proteins transferring and lactoferrin. These glycoproteins bind iron tightly and transport it to specific mammalian receptors. Since iron is bound up by the mammalian host in these ways, the available supply to infecting microorganisms is limited, a factor which can prevent microbial growth. In fact, a positive correlation has been made between successful infection by microorganisms which grow extracellularly and their ability to acquire iron from host proteins. Thus, iron acquisition by pathogenic bacteria has been recognized as a virulence factor.

The concentration of free iron in human serum is low: $10^{-18}M$. This concentration is too low for iron to enter bacteria by passive diffusion, for which a concentration of at least $10^{-6}M$ is required. To circumvent this problem, bacteremic strains elaborate and transport siderophores, which are small molecules that chelate $Fe+3$. The elaboration of siderophores appears to enhance the virulence of bacteremic strains, whereas siderophore expression is apparently not required for invasion or extracellular growth of surface or intracellular pathogens. Therefore, the iron uptake system of bacteremic strains may furnish an effective target for novel antibacterial agents.

Enteric organisms synthesize a variety of siderophores which are utilized for iron transport. Furthermore, they can make use of many siderophores produced by other microorganisms, such as fungi. The system is complex, involving synthesis of the siderophore, secretion of the siderophore, formation of the iron-bound form (ferrisiderophore), binding of the ferrisderophore to receptors on the cell surface, transport of the ferrisiderophore back into the cell followed by the release of $Fe+2$ into the cytoplasm.

In *E. coli* and *Salmonella*, the genes responsible for the synthesis of siderophores, receptors, and their transport encompass a number of operons in the chromosome. These operons are under negative regulation by the Fur repressor protein. The Fur protein uses $Fe+2$ as an aporepressor, so that when iron is in short supply, repression is relieved and iron transport genes are synthesized in large quantity.

Because enteric organisms synthesize and utilize a large number of siderophores to acquire iron, it is necessary to identify a molecule(s) common to all of these systems in order to design a screen that identifies agents that prevent iron transport. The TonB protein represents a suitable target. This protein is required for the translocation of ferrisiderophores, vitamin B12, and certain colicins from outer membrane receptors to the inside of the cell. It is also required for the irreversible adsorption (and therefore, successful infection), of some phages, such as T1 and $\phi$80, to the cell surface. The phenotype of tonB- mutants has provided the tools to set up an assay to target this protein. The phenotypes associated with tonB- mutants are 1) they are deficient in all high-affinity iron-transport systems, 2) they are deficient in transport of vitamin B12, 3) they are resistant to phages T1 and $\phi$80, 4) they are resistant to a variety of colicins, 5) they are resistant to sideromycins such as albomycin, 6) they are sensitive to chromium, 7) they hyperexcrete enterchelin, and 8) they cannot survive in low-iron medium (less than $10^{-6}M$).

The 36K TonB protein is thought to be anchored in the inner membrane and extend into the periplasmic space. Interestingly, iron receptor proteins and colicins which require TonB for transport share a consensus 5 amino acid sequence, the TonB box, which is thought to interact with the amino terminal portion of the TonB protein. This information suggested to us a synthetic structure which apparently inhibits TonB activity.

This invention provides a primary assay, the TonB assay, which is designed to identify fermentation broths or purified compounds which may contain anti-TonB activity. Such activities are potentially antibacterial, since TonB protein is required for successful bacteremic infections. The assay is based on the phenotype of the tonB- mutants, in that an anti-TonB activity would be expected to confer upon cells the same phenotype as that exhibited by a tonB-mutant. In addition, a synthetic molecule which appears to inhibit TonB activity in culture is described.

SUMMARY OF THE INVENTION

The present invention relates to a two-step screening-procedure for identifying a putative TonB inhibitor, the method comprising: (a) growing a TonB+host cell in the presence of a sample believed to contain a TonB inhibitor, and determining as positive or negative the sample's ability to rescue the host cell from a normally growth-inhibiting activity mediated by TonB; (b) growing a TonB+ host cell on a low-iron medium, in the presence of a sample determined to be positive in (a), and observing the presence or absence of growth inhibition of the host cell, whereby the occurrence of growth inhibition on a low iron medium indicates the presence of a putative TonB inhibitor in the sample. This identification of putative TonB inhibitors provides potential antibiotic candidates.

The invention also identifies a novel inhibitor of the TonB protein. The pentapeptide Gly-Thr-Val-Ile-Val/-SEQ I;)NO;1) is shown to inhibit several TonB dependent processes. The pentapeptide provides a positive control for use in the assay as well as providing the basis for design of novel antibiotic molecules.

DETAILED DESCRIPTION OF THE INVENTION

The TonB protein is known to be involved in a number of other activities in addition to the iron transport function; these include transport of Group B colicins into the cell, vitamin B12 transport and successful infection by phages such as $\phi$80 and T1 (Nielands, J. B., *Ann. Rev. Microbiol.*, 36:285–309, 1982). Iron transport is the function of greatest interest in developing an antibiotic: a compound which inhibits the TonB activity should effectively inhibit bacterial growth in vivo, since this function is essential to survival in the ambient low-iron conditions found in animal tissue. Theoretically, a screen designed to detect only this iron-transport inhibiting activity should be effective in identifying potential antibiotic candidates. Mowever, in practice a single step screen based on this activity can be quite difficult to implement. Controlling a plate environment at low-iron levels with little or no source of exogenous iron, is highly labor-intensive and inefficient. Ultimately, if conditions are not precisely correct, false negatives result. Since any successful screening program relies in maintaining a high throughput of test samples, it is desirable that the screen be one that is relatively easily adapted to testing a high volume of samples. An assay based solely on observation of presence or absence of growth in a low-iron medium is simply not practical for these purposes.

In order to overcome this difficulty, the present invention provides a two-step assay more readily adapted to the high throughput required for commercial drug screening. In the present method, a first step involves evaluating the ability of the test sample to "rescue" a TonB containing host cell from one of the otherwise detrimental activities of the TonB protein. For example, infection by various phages, which is mediated by TonB, is typically lethal to the infected host cell. Similarly, the TonB mediated transport of Group B colicins is also typically lethal to the host cell. Evaluating a test sample's ability to rescue the host cell from any of these lethal effects is a good initial indicator of that sample's ability to interfere with the TonB function of phage or colicin transport, and therefore is indicative of the presence of a TonB inhibitor in the sample. It also has the advantage of being capable of being conducted in an iron-containing medium, thereby making it readily adaptable to high volume first-stage screening.

In a preferred embodiment, the first step comprises evaluating rescue from two colicins from different groups. There are four groups of colicins currently known to be transported by TonB: E group colicins, colicins Ia, Ib and V, colicin M, and colicins B and D. An observed rescue effect can be explained in more than one way: it may, as predicted, indicate an inhibition of TonB activity, but it may alternately be the result of interference with the lethal agent's outer membrane receptor. The latter effect will give a false positive lead by indicating rescue, but not by the desired route. Different colicin groups, however, have different receptors; the probability of a test sample's interfering with two different receptors is less than the probability of interfering with only one. Therefore, an observed rescue in the presence of two different colicins selected from distinct groups is a more reliable indicator of an actual inhibition of the TonB protein, than would be rescue in the presence of a single colicin.

A positive result, i.e., a rescue, indicates the presence of a compound or compounds in a test sample which has potential as an inhibitor of the TonB protein. These positive samples are then carried into the second step of the assay, i.e., the zone of inhibition assay. By this point, the number of candidate antibiotics has been narrowed down considerably to only those which have proven effective in the rescue assay. At this stage, since the majority of candidates have been eliminated, the more cumbersome low-iron medium assay can be employed to confirm an anti-TonB activity of the initially positive samples.

Low-iron media can be prepared by treatment with a chelator which will complex all available free iron. For example, dipyridyl in the growth medium will bind iron, as will pretreatment of plates with Chelex TM 100 resin (BioRad, Richmond, CA). Mowever, any iron chelator can be used for this purpose. Growth of E. coli tonB- will be inhibited at $Fe^{3+}$ concentrations of less than $10^{-6}M$, which is thus considered a low-iron medium. A functional TonB protein will permit growth on even a low iron medium. However, in the presence of a TonB inhibitor, there will be growth inhibition on a low iron medium. A TonB- phenotype serves as standard for identifying a suitable low-iron medium: such microorganism cannot grow in the absence of free iron in the medium. Growth inhibition of TonB is determined by comparison with a TonB- phenotype. Strains are available, for example, at the E. coli Genetic Stock Center, Yale University. In the presence of an inhibitory compound, a TonB+ growth pattern on low iron medium will be the same as that of a TonB- organism. Thus, the TonB+ organism is contacted with the test sample previously tested as positive in the rescue assay, on a low iron medium; if the TonB+ cells continue normal growth, there is no TonB inhibition; if the growth is inhibited, the test sample is positive for a TonB inhibitor. A positive result in both the rescue assay and the zone of inhibition assay indicates the sample contains a TonB inhibitor, thereby identifying a potential antibiotic candidate. In cases in which a simple tests positive in the rescue assay and even slightly positive in the inhibition assay, it may be desirable to treat the sample with dipyridyl before retesting in the inhibition assay. This will prevent interference from any of the contaminating free iron in the test sample which could prevent formation of a zone of inhibition on low-iron medium.

As a final confirmation, samples which are positive in both assays may be tested for siderophores, which can give a positive result in both assays, but which are not the desired antibiotic compounds. To assay for presence of siderophores, the sample is spotted on a CAS medium plate, as described in Fekete et al. (Appl. Env. Microbiol., 55:2720-2722, 1989). An orange color produced on the CAS plate indicates the presence of a siderophore in the sample.

The ability of the assay to detect inhibitory compounds is tested with a synthetic TonB box pentapeptide. The sequence Gly-Thr-Val-Ile-Val (SEQ ID NO: 1) represents a conserved sequence found in TonB dependent colicins and receptors, and is thought to interact physically with the TonB protein (Heller et al., Gene 64:147-153, 1988; Schoffler et al., Mol. Gen. Genet. 217:378-383, 1989). The pentapeptide is tested in the two-step assay and found to inhibit infection by phage $\phi$80, colicin killing and cell growth in low iron medium, while two random control pentapeptides have no anti-TonB activity. This pentapeptide thus can serve as a positive control in the assay, and also serve as a root molecule for antibiotic development.

The invention is further illustrated in the following non-limiting examples.

EXAMPLES

1. Rescue Assay

Colicins are prepared by growing overnight cultures of producing strains BZB2102 and ColIa (Colicin B and Colicin Ia, respectively, obtained from Nigel Curtis). Cultures are diluted 1:100 in LB and incubated with Shaking at 37° C. to a Klett of 50-75. Mitomycin C (Sigma) is added to a concentration of 1 $\mu$g/ml and cultures incubated with shaking at 37° C. for an additional 2 hours. Cultures are centrifuged for 10 minutes at 5,000 rpm. The culture pellets are resuspended in 2% of the original volume in 0.9% saline and sonicated for 2-3 minutes in 15-second pulses. Cells are kept cold during sonication. After sonication, the cultures are centrifuged at 7000 rpm for 10 minutes. The supernatant is saved, and centrifuged at 40,000 rpm for 2 hours. The supernatant, containing colicins, is removed, aliquoted and frozen at −70° C. until needed.

The potency of the colicins must be tested prior to use in the assay. A culture lawn of a sensitive *E. coli* strain is grown in LB medium to a Klett of 50 (green filter), and a LB soft agar overlay to make the lawn. The lawns are overlaid with various dilutions of the colicins to be tested in LB soft agar, and incubated overnight. Preferably, the lowest dilution of colicin that results in complete killing of the lawn (excepting scattered colicin-resistant mutants) is used in the rescue assay.

The ability of a test sample to inhibit the killing action of colicins is first determined. LB agar plates (Miller, J. H., Experiments in Molecular Genetics, Cold Spring Harbor Laboratories, N.Y.) are prepared in 150 mm petri dishes. *E. coli* strain H455 aro+ is grown in LB medium at 37° C. to a Klett reading of 50 (green filter). Strain H455 is a wildtype type *E. coli* K12; originally aro−, that was converted to aro+ by P1 transduction.

purposes of this assay; the low-iron classification is confirmed by the inability of tonB− mutants to grow on this medium Strain M1252, which contains a non-revertable tonB− mutation created by insertion mutagenesis is streaked out to single colonies on a low and a high iron plate. It should grow on the high iron and not the low iron medium.

An overnight culture of H455 aro+ is grown in LB medium, pretreated with Chelex®100 resin prepared according to package directions, at 37° C. The next day, the culture is diluted into chelex treated LB medium and grown at 37° C. to a Klett of 50. LB and LB dipyridyl plates are overlaid with 0.25 ml *E. coli* H455 aro+ in 2.5 ml LB top agar pretreated with chelex resin. The agar is allowed to harden; 10 μl of the sample to be tested is then spotted on both an LB and an LB dipyridyl plate and incubated overnight at 37° C. Positive compounds produce a zone of inhibition on the dipyridyl containing plate, but not on the LB plate without dipyridyl. This result is consistent with inhibition of TonB, which is only required for survival in low-iron medium.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

Glu    Thr    Val    Ile    Val
1                            5

Using 96-pen sterile Clonemasters, test samples are picked up and delivered to LB plates, and the plates incubated at room temperature for 30 minutes. 0.25 ml *E. coli* H455 aro+ is added to 8 ml LB soft agar and overlaid the agar assay plate. The plate is left to harden for 5 minutes, then incubated at 37° C. for 60 minutes. Plates are then overlaid with colicins B and Ia in 8 ml LB soft agar. The plates are left to harden and incubated at 37° C. Plates are read after one day and positives circled (positives are identified as zones of *E. coli* growth around areas of broth inoculum, which represent rescue of *E. coli* from colicin inhibition). Plates are reincubated and read again on day two. Positives are scored liberally, and retested. Confirmed positives are then tested in the inhibition assay.

2. Inhibition Assay

Petri plates are prepared with LB medium and LB medium containing 100 mM dipyridyl. Dipyridyl plates are prepared at least one day in advance to allow time for binding of dipyridyl to available iron. LB treated with dipyridyl constitutes, "low-iron" medium for the

What we claim is:

1. A method for identifying a TonB inhibitor in a test sample comprising:
   (a) growing a TonB+ microorganism in the presence of the test sample and, an agent known to be lethal to said microorganism; the lethal activity of said agent being mediated by TonB;
   (b) identifying as positive a test sample with which the lethal activity of the agent is not observed;
   (c) growing on a low-iron medium said TonB+ microorganism in the presence of the test sample identified as positive in (b);
   (d) confirming as positive a test sample with which growth inhibition of the microorganism on the low-iron medium of (c) is observed.

2. The method of claim 1 in which the lethal agent is a colicin or a phage.

3. The method of claim 1 in which the lethal agent is more than one colicin, each colicin being selected from a different class of B Group colicins, the colicins being selected from the group consisting of colicins Ia, Ib and V; colicin M; and colicins B and D.

4. The method of claim 1 in which the microorganism in step (c) is grown in a dipyridyl treated medium.

5. The method of claim 1 in which the low-iron medium contains between 0 and $1 \times 10^{-6}$ M free iron.

6. A TonB inhibitory composition comprising a penta-peptide having the sequence of seq. I.D. No. 1.

7. A method for identifying a TonB inhibitor in a test sample comprising:

(a) growing a TonB+ microorganism in the presence of the test sample and two colicins known to be lethal to said microorganism from two different colicin groups, the activity of said colicin being mediated by TonB;

(b) identifying as positive a test sample with which the lethal activity of the colicin is not observed;

(c) growing on a low-iron medium said TonB+ microorganism in the presence of the test sample identified as positive in (b);

(d) confirming as positive a test sample with which growth inhibition of the microorganism on the low-inner medium of (c) is observed.

8. The method of claim 7 in which the colicins are selected from the B group colicins consisting of colicins Ia, Ib and V; colicin M; and colicins B and D.

9. The method of claim 8 in which the colicins are colicin Ia and colicin B.

* * * * *